(12) United States Patent
Inglis

(10) Patent No.: US 6,554,887 B1
(45) Date of Patent: Apr. 29, 2003

(54) CONTAINMENT DEVICE FOR VAPOR PHASE TRANSFER MATERIALS

(75) Inventor: John T. Inglis, Jupiter, FL (US)

(73) Assignee: Autopax, Inc., Jupiter, FL (US)

( * ) Notice: Subject to any disclaimer, the term of this patent is extended or adjusted under 35 U.S.C. 154(b) by 279 days.

(21) Appl. No.: 09/639,026

(22) Filed: Aug. 15, 2000

(51) Int. Cl.$^7$ ................................................ B01D 46/00
(52) U.S. Cl. ........................ 96/222; 206/484.1; 239/53; 239/56; 239/57; 428/905
(58) Field of Search .............................. 239/56, 53, 54, 239/55, 57, 66; 428/905; 206/484.1, 484.2; 261/DIG. 17; 96/222

(56) References Cited

U.S. PATENT DOCUMENTS

| | | | |
|---|---|---|---|
| 2,626,833 A | * | 1/1953 | Valentine |
| 3,685,734 A | * | 8/1972 | Paciorek et al. |
| 3,896,995 A | | 7/1975 | Lelicoff |
| 4,094,119 A | | 6/1978 | Sullivan |
| 4,145,001 A | | 5/1979 | Weyenberg et al. |
| 4,161,283 A | * | 7/1979 | Hyman |
| 4,285,468 A | * | 8/1981 | Hyman |
| 4,356,969 A | * | 11/1982 | Obermayer et al. |
| 4,419,396 A | | 12/1983 | Sugimoto |
| 4,529,125 A | * | 7/1985 | Sullivan |
| RE32,513 E | | 10/1987 | Seaber et al. |
| 4,874,129 A | * | 10/1989 | DiSapio et al. |
| 4,923,119 A | * | 5/1990 | Yamamoto et al. |
| 5,071,704 A | * | 12/1991 | Fischel-Ghodsian |
| 5,395,047 A | * | 3/1995 | Pendergrass, Jr. |
| 5,518,790 A | * | 5/1996 | Huber et al. |
| 5,637,401 A | * | 6/1997 | Berman et al. |
| 5,743,942 A | * | 4/1998 | Shelley et al. |
| 5,804,264 A | * | 9/1998 | Bowen |
| 6,358,577 B1 | * | 3/2002 | Bowen et al. |

OTHER PUBLICATIONS

US 3,815,838, 6/1974, Engel (withdrawn)

* cited by examiner

*Primary Examiner*—Duane S. Smith
(74) *Attorney, Agent, or Firm*—McHale & Slavin, P.A.

(57) ABSTRACT

A multi-layer package structure useful for vapor phase transfer in an ambient atmosphere, wherein said package protects sensitive contents placed therein such as a desiccant, deodorizer or perfumer by containing the product between a vapor impermeable backing layer, a vapor permeable flexible layer, and a vapor impermeable cover layer. The two outer layers of the package are impermeable to both the contents of the package and the exterior atmosphere, preventing the diffusion of the contents into the atmosphere and protecting the package contents from the outside atmosphere. Upon opening the package by separating the peelable impermeable front web from the permeable layer or membrane the vapors from the from the contents are now free to move through the permeable web into the atmosphere.

9 Claims, 4 Drawing Sheets

---

FRONT
PRINTING PER CLIENTS SPECIFICATIONS
POLYESTER/POLY/FOIL/POLY WEB
REGISTERED PRINTED PEELABLE HOT HEAT SEAL COATING

MIDDLE
PERMEABLE MEMBRANE
PERMANENT HEAT SEAL COATING

BACK
POLYESTER/POLY/FOIL/POLY WEB
PRINTING PER CLIENTS SPECIFICATIONS

*FIG. 4*

FRONT   MIDDLE   BACK

PRINTING PER CLIENTS SPECIFICATIONS
POLYESTER/POLY/FOIL/POLY WEB
REGISTERED PRINTED PEELABLE HOT HEAT SEAL COATING

PERMEABLE MEMBRANE
PERMANENT HEAT SEAL COATING

POLYESTER/POLY/FOIL/POLY WEB
PRINTING PER CLIENTS SPECIFICATIONS

CONTAINMENT DEVICE FOR VAPOR PHASE TRANSFER MATERIALS

FIELD OF THE INVENTION

This invention relates to a containment device, more particularly a flexible package structure for the containment and protection of volatile substances, and most particularly to a containment device capable of providing a controllable and/or predetermined rate of ingress/egress between the ambient environment and the contents therein over a particular period of time.

BACKGROUND OF THE INVENTION

Various environmental considerations make it highly desirable to control the internal atmospheric conditions within a designated area. Illustrative of those areas which are contemplated by the instant invention are the area within a room or vehicle, the area within a piece of furniture, for example in a drawer, within storage containers or storage facilities, and the like.

The type of control desired may require the release of a relatively volatile chemical agent that can function as an air freshener, an aromatizing material, an odor maskant, a pesticide, a pest repellant, an animal repellant, a herbicide, a pheromone, a disinfectant, a sterilizing agent or the like.

Alternatively, it may be desirable to expose the ambient atmosphere to a substance which has absorbtive or adsorbtive functionality. Illustrative of such substances are dessicants, odor sorbents, e.g. activated carbon, silica gel or the like. In certain contemplated embodiments, the active agent may be imbedded in a carrier and is activated by absorption of moisture from the ambient environment, whereupon the activated imbedded material is subsequently dispersed.

DESCRIPTION OF THE PRIOR ART

U.S. Pat. No. 4,145,001 discloses a package which contains plural layers wherein a quantity of a deodorizing material is sandwiched between the layers. The outer layers are taught as being impermeable to the substance and its vapors, thereby preventing escape of the vapors so long as the package is sealed. To open the package the user delaminates two selected layers such that the volatile substance is covered only on one side by a layer which is permeable to the vapors, thereby providing for a controlled release of the substance. In order to function, this patent requires an outer impermeable layer, termed a "release layer" which is selected so as to form only a weak heat bond with the permeable layer. This type of seal allows the release layer to be removed without damaging the other seals. See column 2, lines 5–31. The patent discusses various useful materials among which are polyethylene, polypropylene, MYLAR polyester, foil and ethylene vinyl acetate.

U.S. Pat. No. RE. 32,513 discloses a hollow container having a partially porous shell entrapping a volatile substance and a process for dispensing said volatile substance. The container is sealed within an impermeable outer container until ready for use at which time the outer container is broken.

U.S. Pat. No. 3,815,828 provides an article for dispensing volatile material as a gas or as a vapor through an imperforate envelope. The construction is such that, over a considerable period of time, the volatile material may permeate the imperforate walls and be distributed to the surrounding atmosphere.

U.S. Pat. No. 3,896,995 provides a flying insect repellant assembly constructed to hold a relatively small pad of a liquid absorbent material which holds the insect repellant thereon. The assembly contains a pressure sensitive adhesive layer covered with a number of pliable protective sheets to protect the assembly from inadvertent contact. When the assembly is placed into use, the pliable protective sheets are removed and the adhesive film is utilized to hold the assembly in a desired location.

U.S. Pat. No. 4,094,119 teaches a method for making a volatile substance wherein a backing material, a reservoir material and a permeable material are fused together to form a composite structure which allows controlled volatilization of a substance held within the reservoir layer. At col. 5, lines 54–65, the patentee discloses the inclusion of a MYLAR polyester sheet, fused via an additional process of sonic welding to the front face to prevent volatilization prior to the time desired. Ease of removal of the MYLAR polyester layer may be controlled by the sonic welding process.

U.S. Pat. No. 4,529,125 is drawn to a volatile substance dispensing device including a reservoir layer having a first and a second side and first and second enveloping layers. The composite article is fused together in a circular shape. The use of the circular shape is deemed to be an improvement over the '119 patent above (by the same patentee).

U.S. Pat. No. 4,419,396 describes a three-dimensional perfumed seal characterized by a vinyl base sheet, an adhesive layer on one surface of the base sheet, a release paper applied to the surface of the adhesive layer, opposite the base sheet, a foam synthetic resin padding material on the surface of the base sheet opposite the adhesive layer, a vinyl covering sheet which sandwiches the padding material in cooperation with the base sheet and having a design printed on one of the opposite surfaces thereof, and a capsulated perfume layer laminated to the covering vinyl sheet at the area where the design is present. The perfume is capsulated and requires that the capsules be rubbed or scratched to release their particular fragrance.

What is lacking in the prior art is a protective laminated package and a process for its manufacture which eliminates the requirement for a separate release layer while providing an outer protective layer which protects the contents in storage and is easily removed at the desired time of activation.

SUMMARY OF THE INVENTION

The instant invention is directed towards a package which is constructed of layers of commonly used flexible packaging materials designed to provide required protection for the contents, wherein the method of construction provides a simple easy opening of the package so the contents can provide their intended function.

Illustrative of these materials are an outer layer component such as polyester, paper, nylon, polypropylene or the like which may be laminated via an adhesive layer or an extruded layer of polyethylene to a material which functions to protect the contents of the package such as a "metalized" and/or SARAN polyvinylidene chloride or similar coated barrier films, e.g. an aluminum foil or other like material of sufficient gauge and vapor impermeability to protect the contents. Said adhesive or extrusion layer must have sufficiently high melt flow characteristics to either weld to the porous membrane and/or to flow in and around interstices of porous membranes and provide a permanent, non-peelable seal between the porous membrane and the back panel of the laminated web.

The resulting laminated composite can then be either slit into two rolls to form the front and back layers of the package, or folded in half, which is generally the preferred method since it allows for easy print registration of the front and back portions of the containment construction. If this is done, the front and the back panels can be later separated, e.g. on a horizontal form fill and seal machine by slitting a narrow strip from the folded edge.

The middle layer is a vapor permeable layer which permits communication between the ambient atmosphere and the active agent. Illustrative of materials from which this layer may be composed are porous or permeable web materials such as TYVEK spunbonded olefin, REMAY polypropylene/polyethylene or CELGARD polypropylene/polyethylene, or a roll of olefin material that has been passed over a "stick roll" which punches minute holes in the web, a film such as an olefin film containing a fine powder, such as a Calcium Carbonate, which has been imbedded therein to create a porous permeable film, or a thermoplastic material compatible with the front and back panels of the pouch so the required heat sealing may take place. (Dupont), REMAY or CElGARD, or a roll of olefin material that has been passed over a "stick roll" which punches minute holes in the web, a film such as an olefin film containing a fine powder, such as a Calcium Carbonate, which has been imbedded therein to create a porous permeable film, or a thermoplastic material compatible with the front and back panels of the pouch so the required heat sealing may take place.

Accordingly, it is an objective of the instant invention to provide a three panel pouch and a method for its construction wherein the pouch functions as a gaseous phase delivery system for materials such as perfumes, dessicants, odor maskers and odor eliminators.

It is a further objective of the instant invention to provide either a one or two station process for manufacturing the three panel pouch.

It is yet another objective of the instant invention to provide a specially formulated peelable adhesive having temperature and pressure tolerances effective to provide one peelable outer layer subsequent to heat welding of the composite structure.

It is a still further objective of the invention to provide a heat sealable composite structure wherein one outer layer is permanently sealed without the use of an adhesive layer.

An additional objective of the instant invention is provision of a compositionally modifiable heat seal composition and structure.

Yet a further objective of the instant invention is the provision of a laminate construction having an easily peelable outer layer, wherein said construction effectively controls moisture migration through the edge of the construction.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE FIGURES

FIG. 4 is a cross-sectional representation of the various layers which form the laminated end-product.

DETAILED DESCRIPTION OF THE INVENTION

In accordance with the instant invention, the package may be fabricated on either a horizontal or vertical "form, fill and seal" (FFS) machine of which there are several on the market. These machines may be modified so the package can be heat sealed in three locations prior to introducing the product into the pouch. This filling must be done between the back panel of the pouch, and the permeable middle layer. The pouch is generally filled through its bottom with the pouch in an upside down configuration. The technique followed by the instant invention utilizes a coated adhesive system, as opposed to the coextrusion techniques commonly used in the prior art, wherein commercially produced laminations are coated on the back side or sealant layer of the front panel with an adhesive structured to bond to the permeable layer which will allow the barrier layer to be peeled from the permeable layer of the package thereby exposing the permeable layer so that gaseous components can migrate through the barrier layer.

The following description is based on using a horizontal FFS such as a BARTELT machine. With slight modifications the same concepts can be realized using a Vertical FFS such as a PRODOPAK machine. To facilitate all of the steps required to produce these three panel pouches easily and cost effectively, an auxiliary unwind stand is further provided.

Figure 1:
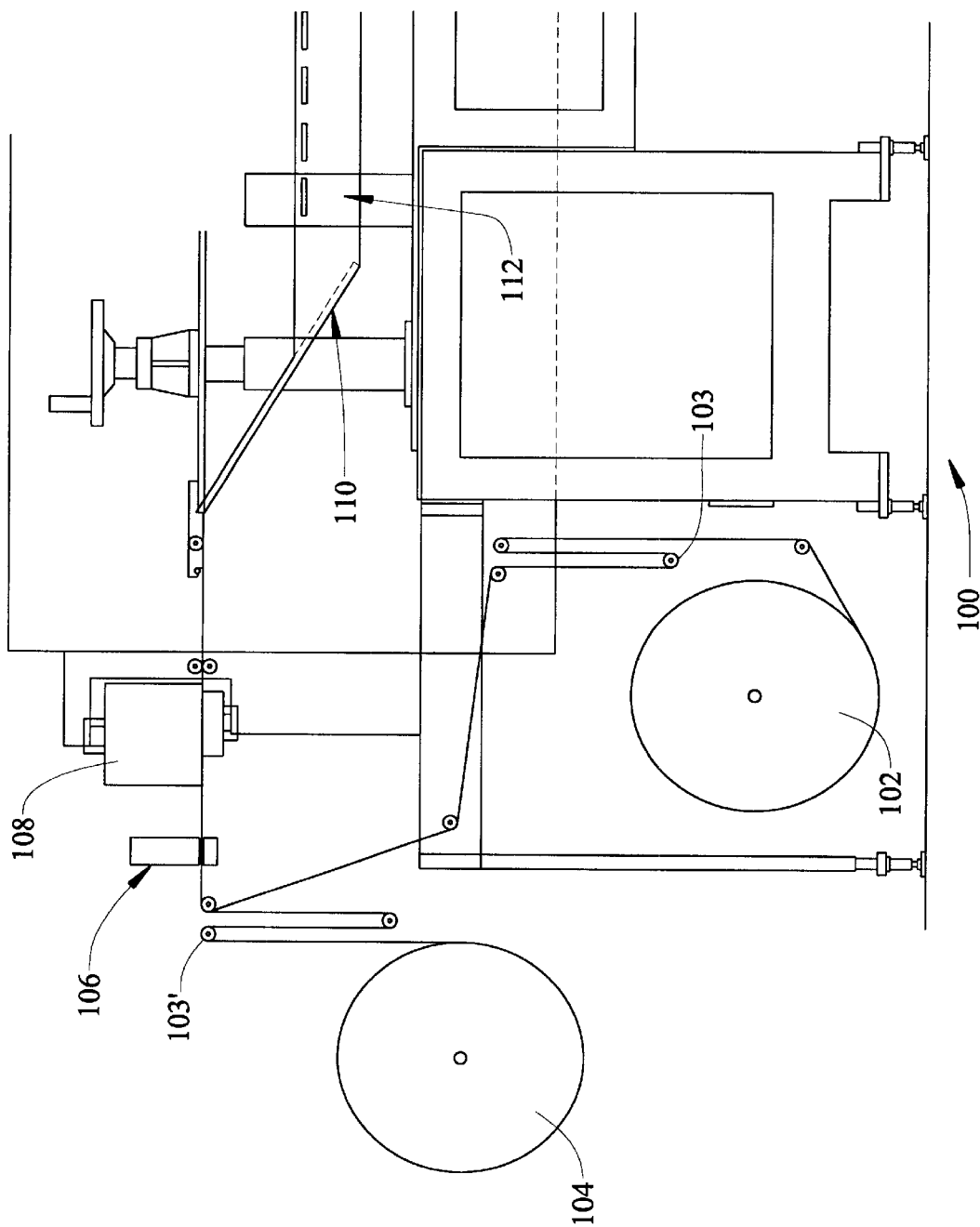
FIG. 1 is a diagrammatic representation of the manufacturing process.

With reference to FIG. 1, a diagrammatic representation of the process 100 is shown. The vapor impermeable foil or barrier web 102 contains both fronts or cover layers and backs or backing layers, with the backs left and fronts right (as particularly set forth in this illustration). To the backing layer portion a first adhering means 101 (see FIG. 2) is attached which is characterized as a sealant film constructed and arranged to provide a permanent bond between the backing layer and the permeable web 104. The first adhering means is preferably a material selected from the group consisting of pressure sensitive adhesives, cold seal adhesives, cohesives, hot melt adhesives, UV curable adhesives, solvent carried heat seals and water carried heat seals.

The shafts on which these rolls are mounted have adjustment mechanisms which allow for movement in the horizontal direction to that the webs 102 and 104 may be aligned one over the other. The material is initially stored at the auxiliary unwind, and is fed via a dancer system 103 which serves to equalize roll tension. Simultaneously the permeable web 104 is fed into the machine, via a similar dancer system 103' and is placed on top of the inside of the back panel. An initial tack is accomplished at heat sealer 106 which seals the inside of the permeable web 104 to the inside of the back panel of the barrier web 102. Subsequent to this step, an optional printer 108 is provided for applying any required warning or instructional information upon the permeable web 104. This is often necessary in situations where a warning is required or instructions for use are needed which might be pulled away and discarded when the cover layer is removed. The permeable web is tack sealed to the inside of the back panel at the top corners of the pouch. This prevents the permeable web from accidentally being pulled away from the inside of the back barrier web and spilling the contents of the pouch when the front panel is peeled away to expose the permeable web. The materials move along to a former/folder 110. In certain embodiments, a tack sealer 112 is provided for attaching the inside of the front of the barrier web to the outside of the permeable web, thus allowing for a positive separation and opening between the inside of the back of the barrier web and the inside of the permeable membrane which is where the contents of the Three-Panel-Pouch must be placed. By tying the permeable membrane to the inside of the front panel, the opening devices that pull the front panel away also pull the permeable panel away from the back barrier web to allow filling between the back barrier web and the permeable membrane.

Figure 2:
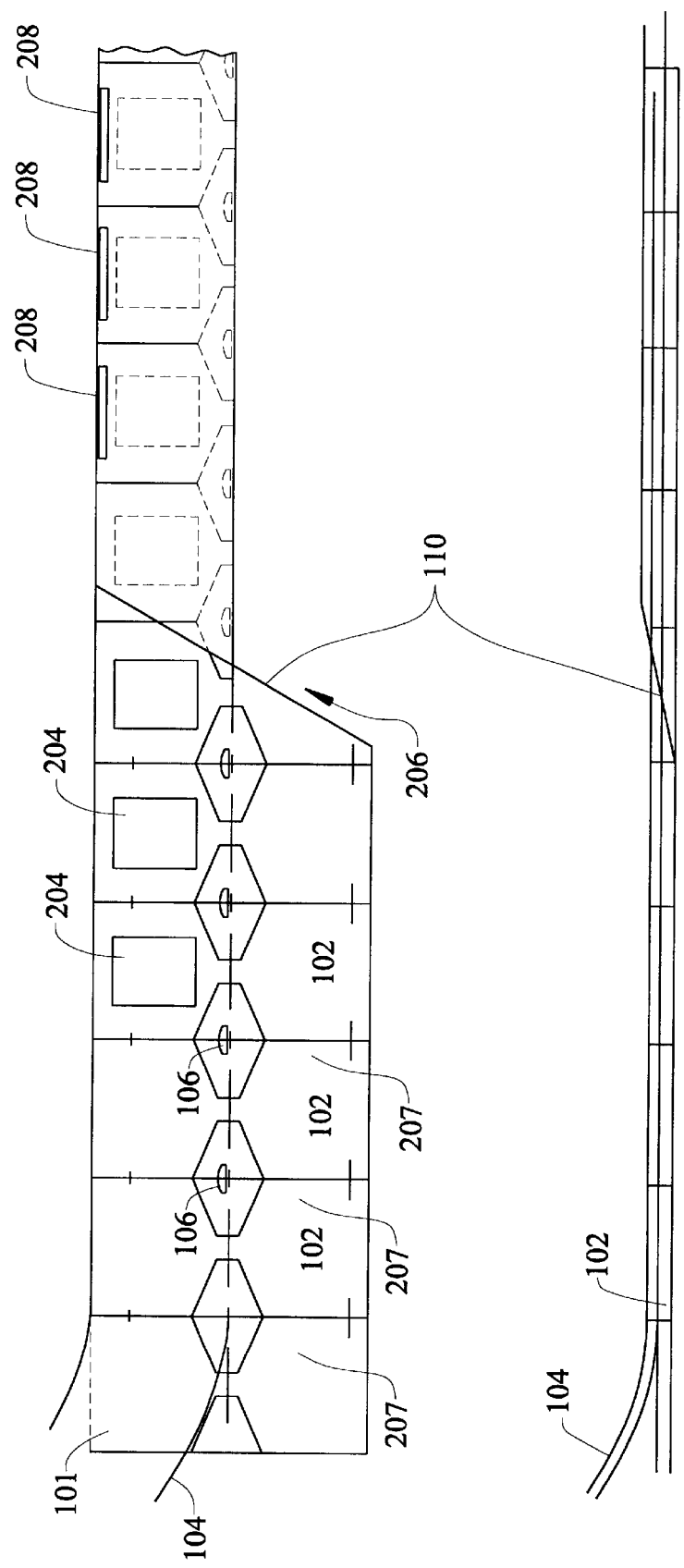
FIG. 2 illustrates an overhead view of the web-sealing process.

Now referring to FIG. 2, an overhead view of the web-sealing process is illustrated. Barrier web fronts and backs 102A and 102B respectively, are illustrated as being fed with the backs left and fronts right when viewed from the rear as they unwind (although this could also be accomplished with fronts left and backs right). The permeable web 104 feeds and is positioned over the backs 102B of the barrier web. The first adhering means 101 is applied to the surface of the backing layer 102B. Tack seals 106 attach the permeable web 104 to the inside of the back panel 102B. The copy block 204 is printed and held in registration by the tack seals 106. At point 206, the web is folded over such that the front panel or covering layer 102A folds down on top of the permeable web 104 and back panel 102B. This covering layer is removably adhered by virtue of a second adhering means 207 applied to the surface thereof, which is a material selected from the group consisting of pressure sensitive adhesives, cold seal adhesives, cohesives, hot melt adhesives, UV curable adhesives, Solvent Carried Heat Seals and Water Carried Heat Seals. In a particularly preferred embodiment, said second adhering means is a blend of an EVA based heat seal emulsion in combination with a wax formulation, said blend being effective to provide a level of bonding, when sealed to said vapor permeable flexible layer, in the range of about 300–1200 grams per inch of width peel strength when sealed at about 350°–450° F., at up to about 0.7 seconds dwell time, at a pressure within the range of about 40–60 PSI. Seals 208 at the bottom of the newly formed pouch seals the inside of the front panel 102A to the outside of the permeable web 104, thus aiding the proper opening of the pouch for filling.

Figure 3A:
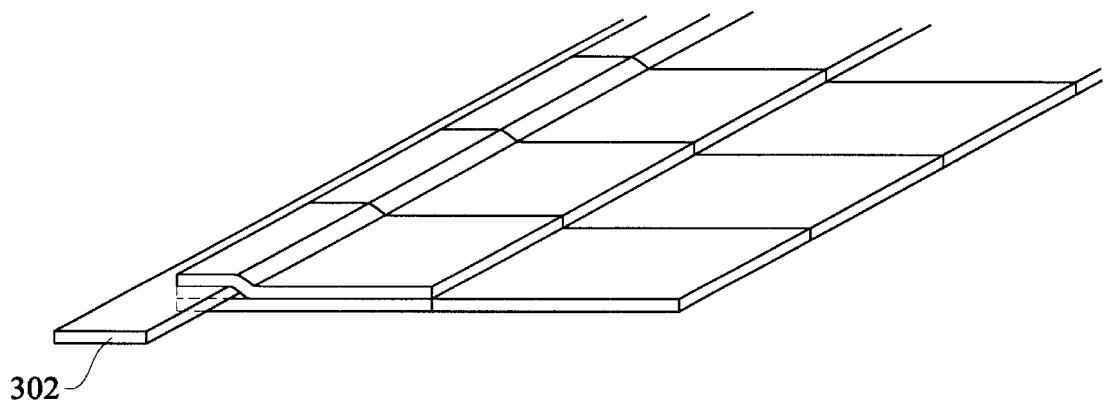
FIGS. 3A, 3B and 3C illustrates an embodiment which utilizes a separator bar in the manufacturing process.
Figure 3B:
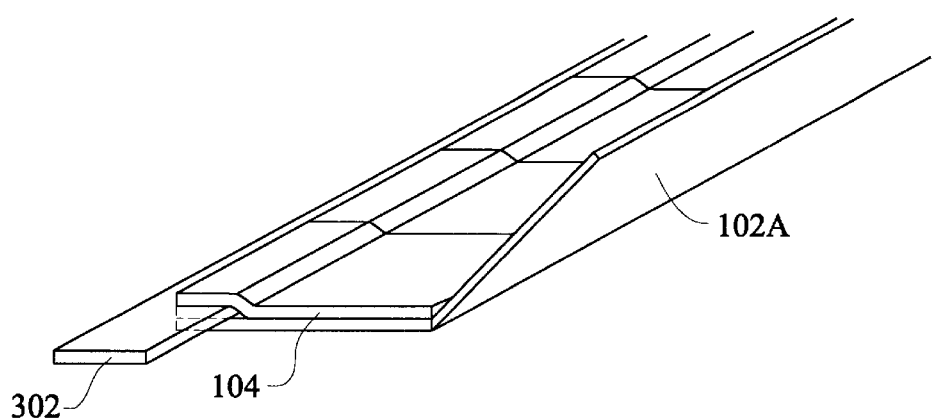
Figure 3C:
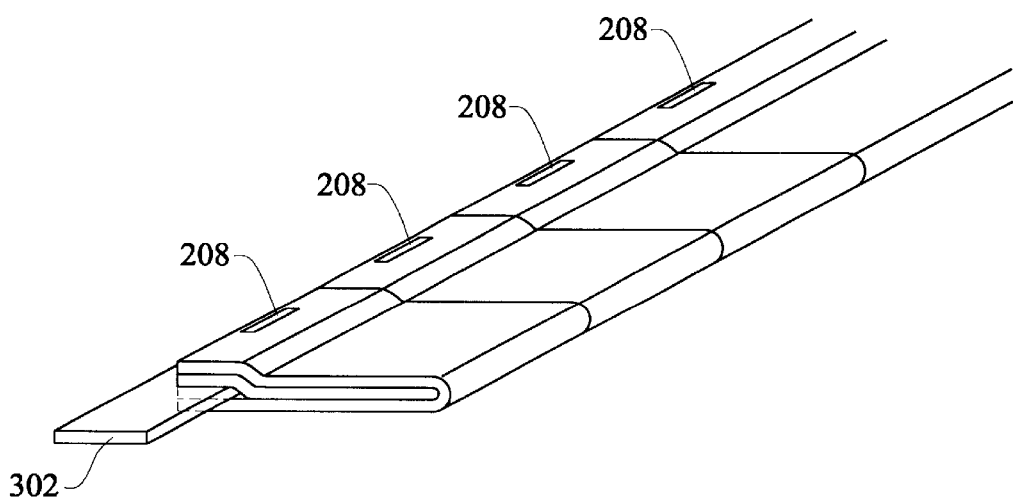

In an alternative embodiment, this separation may be attained with a separator bar as is particularly described in FIGS. 3A, 3B and 3C. As shown in FIG. 3A, the separator bar 302 is positioned so the inside of the back panel tracks underneath the separator bar, and both the permeable web and front panel stay on top of that bar. Moving on to FIG. 3B the barrier front 102A folds over the permeable web 104. Finally, as shown in FIG. 3C, strip seals 208 are formed adhering the inside front of the barrier web 102A to the outside of the permeable web 104.

Now with reference to FIG. 4, a cross-sectional representation of the various layers which are used to form one embodiment of laminated end-product. As indicated, the front or covering layer contains an outermost printed layer printed on the outside polyester layer of a Polyester/Poly/Foil/Poly web followed by a registered applied peelable heat seal coating on the inside of the front panel. The middle layer is a permeable membrane. Lastly, the backing layer contains a polyester/poly/foil/poly web which normally contains printed indicia on the outside of the polyester layer.

In all embodiments, the invention utilizes a specially formulated heat seal coating approach having the ability to function within a wide range of temperature, time and pressure variables. This functionality is capable of accommodating a variety of different webs, e.g. foil and permeable, which often require significantly different heat sealing parameters. The variability of the formulation further compensates for deviations in the gauge inherent to different laminate component combinations.

Common components of the laminations include:
I. An Outer Ply Including
   1. an oriented or non-oriented polyester film, e.g. 37,48 or 100 gauge film, for example a MYLAR polyester film available from
   a paper layer, e.g. 25,35,50 pounds/ream coated or non-coated calendared or non-calendared stock; and
   an oriented polypropylene, e.g. 40,60,100 or 150 gauge such as that supplied from Exxon or Mobil.
II. An Adhesive Ply Including
   1. Two-part curing adhesives such as polyurethanes available from suppliers such as Morton/Rohm and Haas;
   2. Extrusion Lamination inclusive of adhesion promoting polymers available from Dow, Exxon, Dupont, etc.
III. A Barrier Ply Including
   1. An aluminum foil, e.g. those available from Reynolds, Alcoa, Revere, Kaiser and Conalco;
   2. A thermoplastic layer taken alone or in the form of a metallized or barrier coated configuration;
IV. A sealant Ply Including
   1. Films having the requisite degree of barrier properties, chemical resistance, seal integrity and processing temperature requirements;
V. A Permeable Ply Including
   1. Permeable webs such as TYVEK spunbound olef in, REMAY polypropylene/polyethylene, porous paper products, PE, PP, and needle stuck films, such as those available from Clopay, and films, usually olefin, made porous by incorporating a fine powder within the film, for example Calcium Carbonate.

The rate of vapor transfer may be controlled, for example by application of coatings which reduce the size of the apertures in the interstices of the fabric, e.g. TYVEK spunbound olefin or REMAY polypropylene/polyethylene; or alternatively by varying the depth of penetration of the cone shaped needles into the base film of the "stick film" material.

Critical to the operation of the invention is the choice of adhesive. Essential to the adhesive's selection is the ability to deliver a clean and easy peel between the permeable layer and the outer layer while simultaneously creating a hermetically sealed package. Adhesives may be selected from pressure sensitive, cold seal, cohesives, hot melts, UV curable, Solvent Carried Heat Seals and Water Carried Heat Seals. Particularly preferred are the Water Carried Heat Seals since they offer the advantages of simpler application at reduced cost, especially for pattern coating; greater environmental acceptance (in comparison to solvent carried adhesive. Application techniques include, but are not limited to air knife, Mayer rod, Flexo Plate and Gravure Cylinder.

The preferred adhesive structure is a high molecular weight interpolymer dispersion modified by inclusion of wax emulsions which function so as to moderate peelability, anti-block and tack characteristics, wetting agents, fillers and anti-foam compounds. The particular criteria which are critical to achieving the appropriate formulations are application ease, drying rate, tack and blocking characteristics, heat seal temperature, time and pressure ranges, peel strength and transferability of adhesive from one panel to another, or alternatively splitting the adhesive between the two panels.

In a particularly preferred embodiment, application is by way of a printing press e.g. a Gravure press with a turn bar or reversing deck which enables both printing and adhesive coating—either patterned or all-over with one pass—so as to make the coating operation more cost effective. The system utilizes a perfecting setup for pattern applying the adhesive to the back sealable side of the front panel in the areas necessary to seal the front panel to the permeable panel. This method allows for a reduction in the required amount of adhesive which results in reduced adhesive costs and a reduction in drying time which leads to increase throughput.

A particularly preferred adhesive composition is a blend of an EVA based heat seal emulsion, e.g. LATESEAL A 7922A from Pierce and Stevens Chemical Company or Rohm and Haas 37R345 in combination with wax emulsions in an amount effective to adjust the level of bonding to within appropriate parameters, e.g. those offering a peel strength when sealed to a permeable web made from various grades of TYVEK, in the range of about 300–1200 grams/inch of width when sealed at about 3500–450° F., at up to about 0.7 seconds dwell time, at a pressure within the range of about 40–60 PSI. A preferred range of operation includes seal peel strength of 400–800 grams/inch, a temperature ranging from 300°–450° F., at dwells from 0.7 sec. to 1.25 sec. and pressures from 40–60 PSI.

Desirable parameters are easy peel, e.g. 500–800 grams per lineal inch of width with a peel rate of 12" per minute—through inseparable bonds where the bonded components are necessarily destroyed by separating and peeling forces.

It is to be understood that while a certain form of the invention is illustrated, it is not to be limited to the specific form or arrangement of parts herein described and shown.

It will be apparent to those skilled in the art that various changes may be made without departing from the scope of the invention and the invention is not to be considered limited to what is shown and described in the specification and drawings.

What is claimed is:

1. An apparatus useful for vapor phase transfer in an ambient atmosphere comprising:

a vapor impermeable backing layer of a material having an inner surface and an outer surface, said inner surface having a first adhering means;

a vapor permeable flexible layer permanently adhered to said inner surface of said backing layer and forming a sealed compartment adapted to contain at least one vapor phase active material;

a vapor impermeable cover layer having an outer surface and an inner surface, said inner surface having a second adhering means, said inner surface being removably adhered to said vapor permeable flexible layer;

whereby separation of said cover layer from said vapor permeable flexible layer permits vapor phase transfer between said at least one vapor phase active material and said ambient atmosphere.

2. The apparatus of claim 1 wherein:

said vapor impermeable backing layer and vapor impermeable cover layer are each formed from a first material selected from the group consisting of polyester, paper, polyamide, polypropylene or a combination thereof in juxtaposed relation to a vapor impermeable second material having a degree of impermeability effective to prevent vapor phase transfer of said active transfer material.

3. The apparatus of claim 1 wherein:

said vapor permeable flexible layer is formed from a material selected from the group consisting of porous or permeable web materials, a perforated impermeable olefinic material, or a combination thereof.

4. The apparatus of claim 3 wherein said porous web material is a fine powder containing film.

5. The apparatus of claim 1 wherein:

said vapor impermeable backing layer and said vapor permeable flexible layer are permanently adhered by said first adhering means which is a sealant film constructed and arranged to provide a permanent bond therebetween.

6. The apparatus of claim 5 wherein said first adhering means is a material selected from the group consisting of pressure sensitive adhesives, cold seal adhesives, cohesives, hot melt adhesives, UV curable adhesives, solvent carried heat seals and water carried heat seals.

7. The apparatus of claim 1 wherein:

said vapor impermeable cover layer and said vapor permeable flexible layer are removably adhered by said second adhering means which is a material selected from the group consisting of pressure sensitive adhesives, cold seal adhesives, cohesives, hot melt adhesives, UV curable adhesives, Solvent Carried Heat Seals and Water Carried Heat Seals.

8. The apparatus of claim 7 wherein:

said second adhering means is a blend of an EVA based heat seal emulsion in combination with a wax formulation, said blend being effective to provide a level of bonding, when sealed to said vapor permeable flexible layer, in the range of about 300–1200 grams per inch of width peel strength when sealed at about 350°–450° F., at up to about 0.7 seconds dwell time, at a pressure within the range of about 40–60 PSI.

9. A process for producing an apparatus useful for vapor phase transfer in an ambient atmosphere comprising:

providing a vapor impermeable backing layer of a material having an inner surface and an outer surface, said inner surface having a first adhering means;

providing a vapor permeable flexible layer permanently adhered to said inner surface of said backing layer and forming a sealed compartment adapted to contain at least one vapor phase active material; and providing a vapor impermeable cover layer having an outer surface and an inner surface, said inner surface having a second adhering means, said inner surface being removably adhered to said vapor permeable flexible layer;

wherein separation of said cover layer from said vapor permeable flexible layer permits vapor phase transfer between said at least one vapor phase active transfer material and said ambient atmosphere.

* * * * *